United States Patent
Barvian et al.

(10) Patent No.: US 6,936,616 B2
(45) Date of Patent: Aug. 30, 2005

(54) PYRIMIDINE MATRIX METALLOPROTEINASE INHIBITORS

(75) Inventors: Nicole Chantel Barvian, Ann Arbor, MI (US); William Chester Patt, Chelsea, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 221 days.

(21) Appl. No.: 10/075,909

(22) Filed: Feb. 13, 2002

(65) Prior Publication Data

US 2002/0151555 A1 Oct. 17, 2002

Related U.S. Application Data

(60) Provisional application No. 60/268,779, filed on Feb. 14, 2001.

(51) Int. Cl.$^7$ .................. A61K 31/541; A61K 31/5377; A61K 31/513; C07D 417/02; C07D 413/02; C07D 43/02

(52) U.S. Cl. .................. 514/256; 514/227.8; 514/235.8; 514/252.14; 544/60; 544/295; 544/315; 544/330; 544/122

(58) Field of Search .............................. 514/256, 227.8, 514/235.8, 252.14; 544/60, 122, 295, 315, 330

(56) References Cited

U.S. PATENT DOCUMENTS

| | | | | |
|---|---|---|---|---|
| 3,118,754 A | * | 1/1964 | Nickell ........................ | 504/243 |
| 4,031,104 A | * | 6/1977 | Bossert et al. ............... | 546/257 |
| 5,068,337 A | * | 11/1991 | Archibald et al. .......... | 514/256 |
| 5,130,317 A | * | 7/1992 | Baader et al. ............... | 514/256 |
| 5,260,323 A | | 11/1993 | Baader et al. | |
| 5,516,775 A | * | 5/1996 | Zimmermann et al. .. | 514/224.2 |
| 5,519,038 A | | 5/1996 | Baader et al. | |
| 5,948,780 A | | 9/1999 | Peterson, Jr. et al. ....... | 514/255 |
| 6,008,243 A | | 12/1999 | Bender et al. ............... | 514/422 |
| 6,080,750 A | * | 6/2000 | Hisaki et al. ................ | 514/275 |
| 2002/0156061 A1 | | 10/2002 | Barvian et al. | |
| 2002/0161000 A1 | | 10/2002 | Barvian et al. | |
| 2003/0078276 A1 | | 4/2003 | Adrianjara et al. | |
| 2003/0087924 A1 | | 5/2003 | Sorenson | |
| 2003/0144274 A1 | | 7/2003 | Bunker et al. | |
| 2003/0229103 A1 | * | 12/2003 | Weithmann et al. ........ | 514/256 |
| 2004/0167120 A1 | * | 8/2004 | Klingler et al. ......... | 514/217.06 |
| 2005/0004111 A1 | | 1/2005 | Klinger et al. ............ | 514/227.5 |

FOREIGN PATENT DOCUMENTS

| | | |
|---|---|---|
| CA | 2082076 | 5/1993 |
| EP | 0 260 057 A2 | 3/1988 |
| EP | 0418797 | 3/1991 |
| EP | 0 418 797 A2 | 3/1991 |
| EP | 0463592 | 1/1992 |
| EP | 0935963 | 8/1999 |
| EP | 1138680 | 10/2001 |
| JP | 04 840783 A | 6/1973 |
| JP | 08 151380 A | 6/1996 |
| WO | 0009485 | 2/2000 |
| WO | 0112611 | 2/2001 |
| WO | WO 01/63244 A1 | 8/2001 |
| WO | 0234726 | 5/2002 |
| WO | 0234753 | 5/2002 |
| WO | WO02/064568 A1 | 8/2002 |
| WO | 02064568 | 8/2002 |
| WO | WO02/064571 A1 | 8/2002 |
| WO | WO02/064080 A2 A3 | 8/2002 |
| WO | WO02/064547 A2 A3 | 8/2002 |
| WO | WO03/032999 A1 | 4/2003 |
| WO | 03049738 | 6/2003 |

OTHER PUBLICATIONS

Takahashi et. al. Chemical Abstract, 1975, vol. 83, No. 21, p. 491, Abstract #178072b.*
Neunhoffer et. al., Chemical Abstract, 1974, vol. 81, No. 25, p. 545, Abstract #169499c.*
Prikazchikova.et. al., Chemical Abstract, 1974, vol. 81, No. 16, p. 150, Abstract #100677s.*
Matsumoto et. al., Chemical Abstract, 1973, vol. 79, No. 10, p. 454, Abstract #66394u.*
Titov et. al., Chemical Abstract, 1972, vol. 77, No. 13, p. 478, Abstract #94976n.*

(Continued)

Primary Examiner—Richard L. Raymond
Assistant Examiner—Tamthom N. Truong
(74) Attorney, Agent, or Firm—Claude F. Purchase, Jr.; Todd M. Grissey; Charles W. Ashbrook

(57) ABSTRACT

Selective MMP-13 inhibitors are pyrimidine derivatives of the formula

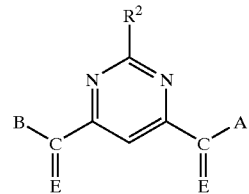

or a pharmaceutically acceptable salt thereof,
wherein:
$R^2$ is hydrogen, halo, hydroxy, $C_1$–$C_6$ alkyl, $C_1$–$C_6$ alkoxy, $C_2$–$C_6$ alkenyl, $C_2$–$C_6$ alkynyl, $NO_2$, $NR^4R^5$, CN, or $CF_3$;
E is independently O or S;
A and B independently are $OR^4$ or $NR^4R^5$;
$R^4$ and $R^5$ independently are H, $C_1$–$C_6$ alkyl, $C_2$–$C_6$ alkenyl, $C_2$–$C_6$ alkynyl, $(CH_2)_n$ aryl, $(CH_2)_n$ cycloalkyl, $(CH_2)_n$ heteroaryl, or $R^4$ and $R^5$ when taken together with the nitrogen to which they are attached complete a 3- to 8-membered ring containing carbon atoms and optionally containing a heteroatom selected from O, S, or NH, and optionally substituted or unsubstituted;
n is an integer of from 0 to 6.

9 Claims, No Drawings

OTHER PUBLICATIONS

Mermann et. al., Chemical Abstract, 1967, vol. 67, No. 13, Abstract #69036s.*
U.S. Appl. No. 10/075,918, Barvian et al., filed Feb. 13, 2002.
U.S. Appl. No. 10/075,069, Adrianjara et al., filed Feb. 13, 2002.
U.S. Appl. No. 10/071,073, Barvian et al., filed Feb. 8, 2002.
U.S. Appl. No. 10/224,234, Sorenson, filed Aug. 20, 2002.
U.S. Appl. No. 10/264,764, Bunker et al., filed Oct. 4, 2002.
U.S. Appl. No. 10/634,531, Johnson, filed Aug. 5, 2003.
U.S. Appl. No. 10/634,709, O'Brien, filed Aug. 5, 2003.
U.S. Appl. No. 10/634,419, Hicks et al., filed Aug. 5, 2003.
U.S. Appl. No. 10/634,713, Picard, filed Aug. 5, 2003.
U.S. Appl. No. 10/739,261, Bunker et al., filed Aug. 5, 2003.
PCT International Search Report for PCT/IB02/00190 filed Jan. 18, 2002.
Chemical Abstracts, vol. 125, No. 13, 1996, Abstract No. 167964d, Fukuda et. al., XP–002198554.
Database Crossfire Bulletin 'Online, Database accession No. 786662, XP–002198556, Beilstein, 1988.
Shkurko, et al, Khim. Geterotsikl. Soedin., 1977; 6; pp 821824—Hard Copy to Follow.
Database Crossfire Bulletin 'Online, Databaase accession No. 7297869, XP–002198557, Beilstein, 1988.
Yamamoto, et al, "Direct Introduction of Acyl and Ethoxycarbonyl, Groups Into Pyrimidine Ring Through the Trimethyl–Stannyl Derivatives" Heterocycles, 1995; 41(6); pp 1275–1290.
Database Crossfire Bulletin 'Online, Database accession No. 139954, XP–002198558, Beilstein, 1988.
J. Chem. Soc., 1959; pp 525–530, Hunt et. al.
Database Crossfire Bulletin 'Online, Database accession No. 791572 XP–002198559, Beilstein, 1988.
Sakasai, et al, "Studies in Pyrimidine Derivatives. XVII. Synthesis of Pyrimidine–4–Carboxylic Esters", Heterocycles, 1979; 13; pp 235–236.
Chemical Abstracts, vol. 79, No. 11, Abstract No. 663944 XP–002198555.
Montana, John, et al, "The design of selective non–substrate–based matrix metalloproteinase inhibitors", Current Opinion in Drug Discovery & Development, 2000; pp 353–361.
Clark, Ian, et al, "Matrix metalloproteinase inhibitors in the treatment of arthritis", Current Opinions in Anti–inflammatory & Immunomodulatory Investigational Drugs, 2000; 2(1), pp 16–25.

Chen, James, et al, "Structure–Based Design of a Novel, Potent, and Selective Inhibitor for MMP–13 Utilizing NMR Spectroscopy and Computer–Aided Molecular Design", J. Am. Chem. Soc., 2000, 122; pp 9648–9654.

Hirota, et al., "Novel Synthesis of Pyrido[3,4–d]pyrimidines, Pyrido[2,3–d]–pyrimidines, and Quinazolines via Palladium–Catalyzed Oxidative coupling", Heterocycles, 1994; 37(1):563–570.

Ye, et al., "Catalytic Domains of Matrix Metalloproteinases: A Molecular Biology Approach to Drug Discovery", Curr.Med.Chem., 1996; 3:407–418.

Lovejoy, et al., "Crystal structures of MMP–1 and –13 reveal the structural basis for selectivity of collagenase inhibitors", Nature Structural Biol., 1999; 6:217–221.

Moy, et al., High–resolution solution structure of the catalytic fragment of human collagenase–3 (MMP–13) complexed with a hydroxamic acid inhibitor, J. Mol. Biol., 2000; 302:671–689.

Mitchell, et al., "Cloning, Expression, and Type II Collagenolytic Activity of Matrix Metalloproteinase–13 from Human Osteoarthritic Cartilage", J. Clin. Invest., 1996: 97(3):761–768.

Neuhold, et al., "Postnatal expression in hyaline cartilage of constitutively active human collagenase–3 (MMP–13) induces osteoarthritis in mice", J. Clin, Invest., 2001; 107:35–44.

Dahlberg, et al., Selective Enhancement of Collagenase–Mediated Cleavage of Resident Type II Collagen in Cultured Osteoarthritic Cartilage and Arrest with a Synthetic Inhibitor that Spares Collagenase I (Matrix Metalloproteinase 1), Arthrit. & Rheum., 2000; 43(3):673–682.

Billinghurst, et al., "Comparison of the Degradation of Type II Collagen and Proteoglycan in Nasal and Articular Cartilages Induced by Interleukin–1 and the Selective Inhibition of Type II Collagen Cleavage by Collagenase", Arthrit. & Rheum., 2000; 43(3):664–672.

Billinghurst, et al., "Enhanced Cleavage of Type II Collagen by Collagenases in Osteoarthritic Articular Cartilage", J. Clin. Invest., 1997; 99:1534–1545.

Office Action mailed Jun. 16, 2003, in U.S. 10/264,764, McKenzie.

* cited by examiner ific MMP
PYRIMIDINE MATRIX METALLOPROTEINASE INHIBITORS

CROSS-REFERENCE TO RELATED APPLICATIONS

This application claims benefit of priority from U.S. Provisional Patent Application No. 60/268,779, filed Feb. 14, 2001.

FIELD OF THE INVENTION

This invention relates to pyrimidine derivatives which inhibit matrix metalloproteinase enzymes and thus are useful for treating diseases resulting from tissue breakdown such as heart disease, multiple sclerosis, osteo- and rheumatoid arthritis, atherosclerosis, and osteoporosis.

BACKGROUND OF THE INVENTION

Matrix metalloproteinases (sometimes referred to as MMPs) are naturally occurring enzymes found in most mammals. Over-expression and activation of MMPs, or an imbalance between MMPs and inhibitors of MMPs, have been suggested as factors in the pathogenesis of diseases characterized by the breakdown of extracellular matrix or connective tissues.

Stromelysin-1 and gelatinase A are members of the MMP family. Other members include fibroblast collagenase (MMP-1), neutrophil collagenase (MMP-8), gelatinase B (92 kDa gelatinase) (MMP-9), stromelysin-2 (MMP-10), stromelysin-3 (MMP-11), matrilysin (MMP-7), collagenase 3 (MMP-13), TNF-alpha converting enzyme (TACE), and other newly discovered membrane-associated matrix metalloproteinases (Sato H., Takino T., Okada Y., Cao J., Shinagawa A., Yamamoto E., and Seiki M., *Nature*, 1994;370:61–65). These enzymes have been implicated with a number of diseases which result from breakdown of connective tissue, including such diseases as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis. A method for preventing and treating these and other diseases is now recognized to be by inhibiting matrix metalloproteinase enzymes, thereby curtailing and/or eliminating the breakdown of connective tissues that results in the disease states.

There is a catalytic zinc domain in matrix metalloproteinases that is typically the focal point for inhibitor design. The modification of substrates by introducing zinc-chelating groups has generated potent inhibitors such as peptide hydroxamates and thiol-containing peptides. Peptide hydroxamates and the natural endogenous inhibitors of MMPs (TIMPs) have been used successfully to treat animal models of cancer and inflammation. MMP inhibitors have also been used to prevent and treat congestive heart failure and other cardiovascular diseases, U.S. Pat. No. 5,948,780.

A major limitation on the use of currently known MMP inhibitors is their lack of specificity for any particular enzyme. Recent data has established that specific MMP enzymes are associated with some diseases, with no effect on others. The MMPs are generally categorized based on their substrate specificity, and indeed the collagenase subfamily of MMP-1, MMP-8, and MMP-13 selectively cleave native interstitial collagens, and thus are associated only with diseases linked to such interstitial collagen tissue. This is evidenced by the recent discovery that MMP-13 alone is over expressed in breast carcinoma, while MMP-1 alone is over expressed in papillary carcinoma (see Chen et al., *J. Am. Chem. Soc.*, 2000;122:9648–9654).

There appears to be few selective inhibitors of MMP-13 reported. A compound named WAY-170523 has been reported by Chen et al., supra., 2000, and a few other compounds are reported in PCT International Application Publication Number WO 01/63244 A1, as allegedly selective inhibitors of MMP-13. Further, U.S. Pat. No. 6,008,243 discloses inhibitors of MMP-13. However, no selective or nonselective inhibitor of MMP-13 has been approved and marketed for the treatment of any disease in any mammal. Accordingly, the need continues to find new low molecular weight compounds that are potent and selective MMP inhibitors, and that have an acceptable therapeutic index of toxicity/potency to make them amenable for use clinically in the prevention and treatment of the associated disease states. An object of this invention is to provide a group of selective MMP-13 inhibitor compounds characterized as being pyrimidine derivatives.

SUMMARY OF THE INVENTION

This invention provides a method for inhibiting matrix metalloproteinase enzymes, and especially MMP-13, using a pyrimidine or analog thereof. The invention is more particularly directed to a method for inhibiting MMP enzymes comprising administering to a host an MMP inhibiting amount of a compound defined by Formula I

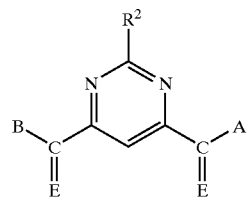

or a pharmaceutically acceptable salt thereof, wherein:

$R^2$ is hydrogen, halo, hydroxy, $C_1$–$C_6$ alkyl, $C_1$–$C_6$ alkoxy, $C_2$–$C_6$ alkenyl, $C_2$–$C_6$ alkynyl, $NO_2$, $NR^4R^5$, CN, or $CF_3$;

E is independently O or S;

A and B independently are $OR^4$ or $NR^5R^6$;

$R^4$ and $R^5$ independently are H, $C_1$–$C_6$ alkyl, $C_2$–$C_6$ alkenyl, $C_2$–$C_6$ alkynyl, $(CH_2)_n$ aryl, $(CH_2)_n$ cycloalkyl, $(CH_2)_n$ heteroaryl, or $R^4$ and $R^5$ when taken together with the nitrogen to which they are attached complete a 3- to 8-membered ring, containing carbon atoms and optionally containing a heteroatom selected from O, S, or NH, and optionally substituted or unsubstituted; and n is an integer from 0 to 6.

Another embodiment of the invention is a method of inhibiting MMP enzymes in a host comprising administering a compound of Formula II

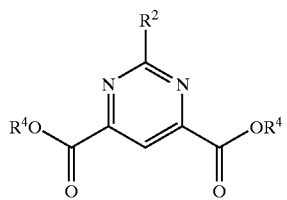

or a pharmaceutically acceptable salt thereof, wherein $R^2$ is as defined above, and each $R^4$ independently is as defined above.

Another embodiment of the invention is a method for inhibiting MMP enzymes comprising administering a compound of Formula III

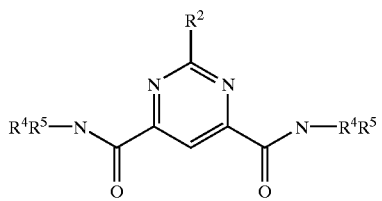

or a pharmaceutically acceptable salt thereof, wherein $R^2$ is as defined above, and each $R^4$ and $R^5$ independently are as defined above.

Another embodiment of the invention is a method for inhibiting MMP enzymes comprising administering MMP inhibitors having Formula IV

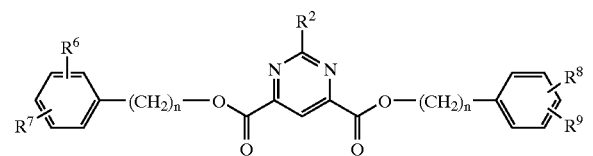

or a pharmaceutically acceptable salt thereof, wherein n and $R^2$ are as defined above, and $R^6$, $R^7$, $R^8$, and $R^9$ independently are hydrogen, halo, $C_1$–$C_6$ alkyl, $C_1$–$C_6$ alkoxy, nitro, or $NH_2$.

Another embodiment of the invention is a method for inhibiting MMP enzymes comprising administering an MMP inhibitor of Formula V

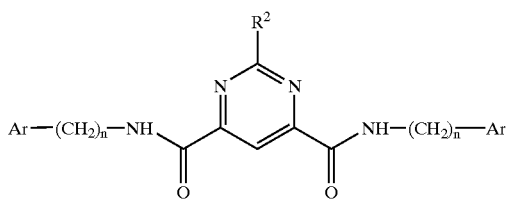

or a pharmaceutically acceptable salt thereof, wherein n and $R^2$ are as defined above, and each Ar independently is aryl or Het, wherein aryl is phenyl or substituted phenyl, and Het is an unsubstituted or substituted heteroaryl group.

Compounds of Formulas I, II, III, IV, and V are provided as further embodiments of this invention.

Another embodiment of the invention are amides of Formula I wherein one or both of A and B is $NR^4R^5$, wherein $R^4$ and $R^5$ are as defined above.

Another embodiment of the invention are compounds selected from:

Pyrimidine-4,6-dicarboxylic acid, (4-chlorobenzylamide), [(1,3-benzodioxol-5-ylmethyl)-amide];

Pyrimidine-4,6-dicarboxylic acid, (4-carboxybenzylamide), [(1,3-benzodioxol-5-ylmethyl)-amide];

Pyrimidine-4,6-dicarboxylic acid, (4-carboxybenzylamide), (4-methoxy-benzylamide);

Pyrimidine-4,6-dicarboxylic acid, (4-carboxybenzylamide), (3-methoxy-benzylamide);

Pyrimidine-4,6-dicarboxylic acid, (4-carbomethoxybenzylamide), (3-methoxy-benzylamide);

Pyrimidine-4,6-dicarboxylic acid, (4-carboxybenzylamide), (3-pyridylmethylamide);

Pyrimidine-4,6-dicarboxylic acid, (4-carboxybenzylamide), (3-thiophenemethylamide);

Pyrimidine-4,6-dicarboxylic acid, (2,1,3-benzothiadiazol-5-ylmethyl) amide, [(1,3-benzodioxol-5-ylmethyl)-amide];

Pyrimidine-4,6-dicarboxylic acid, (2,1,3-benzooxadiazol-5-ylmethyl) amide, [(1,3-benzodioxol-5-ylmethyl)-amide];

Pyrimidine-4,6-dicarboxylic acid, (2,1,3-benzothiadiazol-5-ylmethyl) amide, (4-methoxy-benzylamide);

Pyrimidine-4,6-dicarboxylic acid, (2,1,3-benzothiadiazol-5-ylmethyl) amide, (3-methoxy-benzylamide);

Pyrimidine-4,6-dicarboxylic acid bis-(1,3-benzodioxol-5-ylmethyl) ester;

Pyrimidine-4,6-dicarboxylic acid, bis-(4-chlorobenzylamide);

Pyrimidine-4,6-dicarboxylic acid, bis-[(1,3-benzodioxol-5-ylmethyl)-amide];

Pyrimidine-4,6-dicarboxylic acid, bis-(4-methoxybenzylamide);

Pyrimidine-4,6-dicarboxylic acid, bis-(3-methoxybenzylamide);

Pyrimidine-4,6-dicarboxylic acid, bis-(4-carboxybenzylamide); and

Pyrimidine-4,6-dicarboxylic acid, bis-(4-carbomethoxybenzylamide).

Another embodiment of this invention is a pharmaceutically acceptable salt of the above-named compounds.

Another embodiment of this invention is a pharmaceutical composition, comprising a compound of Formula I, or a pharmaceutically acceptable salt thereof, admixed with a pharmaceutically acceptable carrier, excipient, or diluent.

Another embodiment of this invention is a pharmaceutical composition comprising a compound of Formulas II, III, IV, or V, or a pharmaceutically acceptable salt thereof, admixed with a pharmaceutically acceptable carrier, excipient, or diluent.

Another embodiment of this invention is a pharmaceutical composition comprising a compound selected from:

Pyrimidine-4,6-dicarboxylic acid, (4-chlorobenzylamide), [(1,3-benzodioxol-5-ylmethyl)-amide];

Pyrimidine-4,6-dicarboxylic acid, (4-carboxybenzylamide), [(1,3-benzodioxol-5-ylmethyl)-amide];

Pyrimidine-4,6-dicarboxylic acid, (4-carboxybenzylamide), (4-methoxy-benzylamide);

Pyrimidine-4,6-dicarboxylic acid, (4-carboxybenzylamide), (3-methoxy-benzylamide);

Pyrimidine-4,6-dicarboxylic acid, (4-carbomethoxybenzylamide), (3-methoxy-benzylamide);

Pyrimidine-4,6-dicarboxylic acid, (4-carboxy-benzylamide), (3-pyridylmethylamide);
Pyrimidine-4,6-dicarboxylic acid, (4-carboxy-benzylamide), (3-thiophenemethylamide);
Pyrimidine-4,6-dicarboxylic acid, (2,1,3-benzothiadiazol-5-ylmethyl) amide, [(1,3-benzodioxol-5-ylmethyl)-amide];
Pyrimidine-4,6-dicarboxylic acid, (2,1,3-benzooxadiazol-5-ylmethyl) amide, [(1,3-benzodioxol-5-ylmethyl)-amide];
Pyrimidine-4,6-dicarboxylic acid, (2,1,3-benzothiadiazol-5-ylmethyl) amide, (4-methoxy-benzylamide);
Pyrimidine-4,6-dicarboxylic acid, (2,1,3-benzothiadiazol-5-ylmethyl) amide, (3-methoxy-benzylamide);
Pyrimidine-4,6-dicarboxylic acid bis-(1,3-benzodioxol-5-ylmethyl) ester;
Pyrimidine-4,6-dicarboxylic acid, bis-(4-chloro-benzylamide);
Pyrimidine-4,6-dicarboxylic acid, bis-[(1,3-benzodioxol-5-ylmethyl)-amide];
Pyrimidine-4,6-dicarboxylic acid, bis-(4-methoxy-benzylamide);
Pyrimidine-4,6-dicarboxylic acid, bis-(3-methoxy-benzylamide);
Pyrimidine-4,6-dicarboxylic acid, bis-(4-carboxy-benzylamide); and
Pyrimidine-4,6-dicarboxylic acid, bis-(4-carbomethoxy-benzylamide), or a pharmaceutically acceptable salt thereof, admixed with a pharmaceutically acceptable carrier, excipient, or diluent.

Another embodiment of this invention is a pharmaceutical composition comprising a pharmaceutically acceptable salt of the above-named compounds, admixed with a pharmaceutically acceptable carrier, excipient, or diluent.

A further embodiment of this invention is a method for treating a disease mediated by an MMP-13 enzyme, comprising administering to a patient suffering from such a disease an effective amount of a compound of Formula I, or a pharmaceutically acceptable salt thereof.

Another embodiment of this invention is a method for treating a disease mediated by an MMP-13 enzyme, comprising administering to a patient suffering from such a disease an effective amount of a compound of Formula II, III, IV, or V, or an above-named compound, or any other above-described compound embodiment, including a compound of Formula I wherein one or both of A and B is $NR^4R^5$, wherein $R^4$ and $R^5$ are as defined above, or a pharmaceutically acceptable salt thereof.

Another embodiment of this invention is a method of treatment according to this invention is treatment of a disease selected from cancer, (especially breast carcinoma), inflammation, osteoarthritis, rheumatoid arthritis, and heart failure, comprising administering to a patient in need thereof a compound of Formula I, or a pharmaceutically acceptable salt thereof.

Another embodiment of this invention is a method of treatment according to this invention is treatment of a disease selected from cancer, (especially breast carcinoma), inflammation, osteoarthritis, rheumatoid arthritis, and heart failure, comprising administering to a patient suffering from such a disease an effective amount of a compound of Formula II, II, IV, or V, or an above-named compound, or any other above-described compound embodiment, including a compound of Formula I wherein one or both of A and B is $NR^4R^5$, wherein $R^4$ and $R^5$ are as defined above, or a pharmaceutically acceptable salt thereof.

A further embodiment is use of a compound of Formula I, or a pharmaceutically acceptable salt thereof, in the manufacture of a medicament for the treatment of a disease mediated by an MMP-13 enzyme. Preferred is use of a compound of Formula I, or a pharmaceutically acceptable salt thereof, wherein one or both of A and B is $NR^4R^5$, wherein $R^4$ and $R^5$ are as defined above. Also preferred is use of a compound of Formula II, III, IV, or V, or a pharmaceutically acceptable salt thereof.

DETAILED DESCRIPTION OF THE INVENTION

The compounds to be used in the method of inhibiting MMP enzymes provided by this invention are those defined by Formula I. In Formula I, $R^1$ to $R^9$ include "$C_1$–$C_6$ alkyl" groups. These are straight and branched carbon chains having from 1 to 6 carbon atoms. Examples of such alkyl groups include methyl, ethyl, isopropyl, tert-butyl, neopentyl, and n-hexyl. The alkyl groups can be substituted if desired, for instance with groups such as hydroxy, amino, alkyl, and dialkylamino, halo, trifluoromethyl, carboxy, nitro, and cyano.

"Alkenyl" means straight and branched hydrocarbon radicals having from 2 to 6 carbon atoms and one double bond and includes ethenyl, 3-buten-1-yl, 2-ethenylbutyl, 3-hexen-1-yl, and the like.

"Alkynyl" means straight and branched hydrocarbon radicals having from 2 to 6 carbon atoms and one triple bond and includes ethynyl, 3-butyn-1-yl, propynyl, 2-butyn-1-yl, 3-pentyn-1-yl, and the like.

"Cycloalkyl" means a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, and the like. Also included are rings in which 1 to 3 heteroatoms replace carbons. Such groups are termed "heterocyclyl," which means a cycloalkyl group also bearing at least one heteroatom selected from O, S, or $NR^2$, examples being oxiranyl, pyrrolidinyl, piperidyl, tetrahydropyranyl, and morpholinyl.

"Alkoxy" refers to the alkyl groups mentioned above bound through oxygen, examples of which include methoxy, ethoxy, isopropoxy, tert-butoxy, and the like. In addition, alkoxy refers to polyethers such as —O—$(CH_2)_2$—O—$OH_3$, and the like.

"Acyl" means an R group that is an alkyl or aryl (Ar) group bonded through a carbonyl group, i.e., R—C(O)—, where R is alkyl or aryl. For example, acyl includes a $C_1$–$C_6$ alkanoyl, including substituted alkanoyl, wherein the alkyl portion can be substituted by $NR^4R^5$ or a carboxylic or heterocyclic group. Typical acyl groups include acetyl, benzoyl, isonicotinoyl, and the like.

The alkyl, alkenyl, alkoxy, and alkynyl groups described above are optionally substituted, preferably by 1 to 3 groups selected from $NR^4R^5$, phenyl, substituted phenyl, thio $C_1$–$C_6$ alkyl, $C_1$–$C_6$ alkoxy, hydroxy, carboxy, $C_1$–$C_6$ alkoxycarbonyl, acyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$–$C_6$ alkyl or $(CH_2)_n$ Ph where n is 1, 2, or 3. Perhalo and polyhalo substitution is also embraced.

Examples of substituted alkyl groups include 2-aminoethyl, acetylmethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, 4-benzoylbutyl, and 2-(4-methylpiperazinyl)ethyl.

Examples of substituted alkynyl groups include 2-methoxyethynyl, 2-benzoylethylyl, 2-ethylsulfanyethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include aminomethoxy, acetoxymethoxy, trifluoromethoxy, 2-diethylaminoethoxy, 2-ethoxycarbonylethoxy, 3-hydroxypropoxy, 6-carboxhexyloxy, and the like.

Further, examples of substituted alkyl, alkenyl, and alkynyl groups include dimethylaminomethyl, carboxymethyl, 4-dimethylamino-3-buten-1-yl, 5-ethylmethylamino-3-pentyn-1-yl, 4-morpholinobutyl, 4-tetrahydropyrinidylbutyl, 3-imidazolidin-1-ylpropyl, 4-tetrahydrothiazol-3-ylbutyl, phenylmethyl, 3-chlorophenylmethyl, and the like.

The terms "Ar" and "aryl" refer to unsubstituted and substituted aromatic groups. Heteroaryl (Het) groups have from 4 to 9 ring atoms, from 1 to 4 ring atoms of which are independently selected from the group consisting of O, S, and N. Preferred heteroaryl groups have 1 or 2 heteroatoms in a 5- or 6-membered aromatic ring. Mono- and bicyclic aromatic ring systems are included in the definition of aryl and heteroaryl. Preferred substituent groups include alkyl, alkoxy, halo, amino, alkylamino, dialkylamino, CN, $CF_3$, thioalkyl, acyl and hydroxy. Typical aryl and heteroaryl groups include phenyl, 3-chlorophenyl, 2,6-dibromophenyl, pyridyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, morpholinyl, indolyl, benzotriazolyl, indazolyl, pyrrole, pyrazole, imidazole, thiazole, methylenedioxyphenyl, benzo-2,1,3-thiadiazole, benzo-2,1,3-oxadiazole, and the like.

Preferred Ar groups are phenyl and phenyl substituted by 1, 2, or 3 groups independently selected from the group consisting of alkyl, alkoxy, thio, thioalkyl, halo, hydroxy, —$COOR^7$, trifluoromethyl, nitro, amino of the formula —$NR^4R^5$, and $T(CH_2)_mQR^4$ or $T(CH_2)_mCO_2R^4$ wherein m is 1 to 6, T is O, S, $NR^4$, $N(O)R^4$, $NR^4R^6Y$, or $CR^4R^5$, Q is O, S, $NR^5$, $N(O)R^5$, or $NR^5R^6Y$ wherein $R^4$ and $R^5$ are as described above, and $R^7$ is hydrogen, alkyl, or substituted alkyl, for example, methyl, trichloroethyl, diphenylmethyl, and the like. The alkyl and alkoxy groups can be substituted as defined above. For example, typical groups are carboxyalkyl, alkoxycarbonylalkyl, hydroxyalkyl, hydroxyalkoxy, and alkoxyalkyl. Typical substituted aryl groups include 2,6-dichlorophenyl, 3-hydroxyphenyl, 1,3-benzodioxolyl, 4-dimethylaminophenyl, 2,4,6-triethoxyphenyl, 3-cyanophenyl, 4-methylthiophenyl, and 3,5-dinitrophenyl.

Examples of $NR^4R^5$ groups include amino, methylamino, di-isopropylamino, acetyl amino, propionyl amino, 3-aminopropyl amino, 3-ethylaminobutyl amino, 3-di-n-propylamino-propyl amino, 4-diethylaminobutyl amino, and 3-carboxypropionyl amino. $R^4$ and $R^5$ can be taken together with the nitrogen to which they are attached to form a ring having 3 to 7 carbon atoms and 1, 2, or 3 heteroatoms selected from the group consisting of nitrogen, substituted nitrogen, oxygen, and sulfur. Examples of such cyclic $NR^4R^5$ groups include pyrrolidinyl, piperazinyl, 4-methylpiperazinyl, 4-benzylpiperazinyl, pyridinyl, piperidinyl, pyrazinyl, morpholinyl, and the like.

"Halo" includes fluoro, chloro, bromo, and iodo.

The term "patient" means a mammal. Preferred patients include humans, cats, dogs, cows, horses, pigs, and sheep.

The term "animal" means a mammal. Preferred animals are include humans, rats, mice, guinea pigs, rabbits, monkeys, cats, dogs, cows, horses, pigs, and sheep.

The phrases "therapeutically effective amount" and "effective amount" are synonymous unless otherwise indicated, and mean an amount of a compound of the present invention that is sufficient to improve the condition, disease, or disorder being treated. Determination of a therapeutically effective amount, as well as other factors related to effective administration of a compound of the present invention to a patient in need of treatment, including dosage forms, routes of administration, and frequency of dosing, may depend upon the particulars of the condition that is encountered, including the patient and condition being treated, the severity of the condition in a particular patient, the particular compound being employed, the particular route of administration being employed, the frequency of dosing, and the particular formulation being employed. Determination of a therapeutically effective treatment regimen for a patient is within the level of ordinary skill in the medical or veterinarian arts. In clinical use, an effective amount may be the amount that is recommended by the U.S. Food and Drug Administration, or an equivalent foreign agency.

The phrase "admixed" or "in admixture" means the ingredients so mixed comprise either a heterogeneous or homogeneous mixture. Preferred is a homogeneous mixture.

The phrases "pharmaceutical preparation" and "preparation" are synonymous unless otherwise indicated, and include the formulation of the active compound with encapsulating material as a carrier providing a capsule in which the active component, with or without other carriers, is surrounded by a carrier, which is thus in association with it. Similarly, cachets and lozenges are included. Pharmaceutical preparations are fully described below.

The phrase "anticancer effective amount" means an amount of invention compound, or a pharmaceutically acceptable salt thereof, sufficient to inhibit, halt, or cause regression of the cancer being treated in a particular patient or patient population. For example in humans or other mammals, an anticancer effective amount can be determined experimentally in a laboratory or clinical setting, or may be the amount required by the guidelines of the United States Food and Drug Administration, or equivalent foreign agency, for the particular cancer and patient being treated.

The phrase "MMP-13 inhibiting amount" means an amount of invention compound, or a pharmaceutically acceptable salt thereof, sufficient to inhibit an enzyme matrix metalloproteinase-13, including a truncated form thereof, including a catalytic domain thereof, in a particular animal or animal population. For example in a human or other mammal, an MMP-13 inhibiting amount can be determined experimentally in a laboratory or clinical setting, or may be the amount required by the guidelines of the United States Food and Drug Administration, or equivalent foreign agency, for the particular MMP-13 enzyme and patient being treated.

It should be appreciated that the matrix metalloproteinases include the following enzymes:

MMP-1, also known as interstitial collagenase, collagenase-1, or fibroblast-type collagenase;

MMP-2, also known as gelatinase A or 72 kDa Type IV collagenase;

MMP-3, also known as stromelysin or stromelysin-1;

MMP-7, also known as matrilysin or PUMP-1;

MMP-8, also known as collagenase-2, neutrophil collagenase, or polymorphonuclear-type ("PMN-type") collagenase;

MMP-9, also known as gelatinase B or 92 kDa Type IV collagenase;

M-10, also known as stromelysin-2;

MMP-11, also known as stromelysin-3;

MMP-12, also known as metalloelastase;

MMP-13, also known as collagenase-3;

MMP-14, also known as membrane-type ("MT") 1-MMP or MT1-MMP;

MMP-15, also known as MT2-MMP;

MMP-16, also known as MT3-MMP;

MMP-17, also known as MT4-MMP;

MMP-18; and

MMP-19.

Other MMPs are known, including MMP-26, which is also known as matrilysin-2.

One aspect of the present invention is compounds of Formula I, or a pharmaceutically acceptable salt thereof, that are selective inhibitors of the enzyme MMP-13. A selective inhibitor of MMP-13, as used in the present invention, is a compound that is ≧5 times more potent in vitro versus MMP-13 than versus at least one other matrix metalloproteinase enzyme such as, for example, MMP-1, MMP-2, MMP-3, MMP-7, MMP-8, MMP-9, or MMP-14, or versus tumor necrosis factor alpha convertase ("TACE"). A preferred aspect of the present invention is compounds that are selective inhibitors of MMP-13 versus MMP-1.

Still other aspects of the present invention are compounds of Formula I, or a pharmaceutically acceptable salt thereof, that are selective inhibitors of MMP-13 versus 2, 3, 4, 5, 6, or 7 other MMP enzymes, or versus TACE and 1, 2, 3, 4, 5, 6, or 7 other MMP enzymes. Other aspects of the present invention are compounds of Formula I, or a pharmaceutically acceptable salt thereof, that are ≧10 times, ≧20 times, ≧50 times, ≧100 times, or ≧1000 times more potent versus MMP-13 than versus at least one of any other MMP enzyme or TACE.

It should be appreciated that determination of proper dosage forms, dosage amounts, and routes of administration, is within the level of ordinary skill in the pharmaceutical and medical arts, and is described below.

The term "$IC_{50}$" means the concentration of test compound required to inhibit activity of a biological target, such as a receptor or enzyme, by 50%.

The phrase "catalytic domain" means the domain containing a catalytic zinc cation of the MMP enzyme, wherein the MMP enzyme contains 2 or more domains. A catalytic domain includes truncated forms thereof that retain at least some of the catalytic activity of MMP-13 or MMP-13CD. For example, the collagenases, of which MMP-13 is a member, have been reported to contain a signal peptide domain, a propeptide domain, a catalytic domain, and a hemopexin-like domain (Ye Qi-Zhuang, Hupe D., Johnson L., Current Medicinal Chemistry, 1996;3:407418).

The phrase "a method for inhibiting MMP-13" includes methods of inhibiting full length MMP-13, truncated forms thereof that retain catalytic activity, including forms that contain the catalytic domain of MMP-13, as well as the catalytic domain of MMP-13 alone, and truncated forms of the catalytic domain of MMP-13 that retain at least some catalytic activity.

It should be appreciated that it has been shown previously (Ye Qi-Zhuang, et al., 1996, supra) that inhibitor activity against a catalytic domain of an MMP is predictive of the inhibitor activity against the respective full-length enzyme.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention.

The compounds of Formula I may have chiral centers, and thus can exist as racemic mixtures and individual enantiomers. All such isomeric forms can be used in the method of this invention and are provided as new compounds.

The compounds of Formula I are capable of further forming both pharmaceutically acceptable formulations comprising salts, including but not limited to acid addition and/or base salts, solvents and N-oxides of a compound of Formula I. This invention also provides pharmaceutical formulations comprising a compound of Formula I together with a pharmaceutically acceptable carrier, diluent, or excipient. All of these forms can be used in the method of the present invention.

Pharmaceutically acceptable acid addition salts of the compounds of Formula I include salts derived form inorganic acids such as hydrochloric, nitric, phosphoric, sulfuric, hydrobromic, hydroiodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge et al., "Pharmaceutical Salts," *J. of Pharmaceutical Science*, 1977;66:1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge et al., supra., 1977.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

The compounds of the present invention can be formulated and administered in a wide variety of oral and parenteral dosage forms, including transdermal and rectal administration. All that is required is that an MMP inhibitor be administered to a mammal suffering from a disease in an effective amount, which is that amount required to cause an improvement in the disease and/or the symptoms associated with such disease. It will be recognized to those skilled in the art that the following dosage forms may comprise as the active component, either a compound of Formula I or a corresponding pharmaceutically acceptable salt or solvate of a compound of Formula I.

The invention compounds are prepared by methods well known to those skilled in the art of organic chemistry. The compounds of Formula I are prepared utilizing commercially available starting materials, or reactants that are readily prepared by standard organic synthetic techniques. A typical synthesis of the invention compounds of Formula I is shown in Scheme 1 below. The first step in Scheme 1 comprises reacting a diacid with a chlorinating reagent such as thionyl chloride or oxalyl chloride in a nonprotic solvent such as dichloromethane (DCM) to give the diacid chloride. This acid chloride can then be reacted with an amine, $NHR^4R^5$, in excess or with an organic base such as triethylamine, to give a bis-amide of Formula I. Alternately, the acid chloride can be reacted with an alcohol, $R^4OH$, in a nonprotic solvent such as dichloromethane along with an organic or inorganic base such as triethylamine or potassium carbonate to give a bis-ester of Formula I. The bis-ester can in some circumstances be reacted with an amine, $NHR^4R^5$, at elevated temperatures to give a bis-amide of Formula I. The diacid can also be reacted with an alkyl halide in a nonprotic solvent containing an organic or inorganic base to give a bis-ester of Formula I. A third sequence involves the reaction of the diacid with hydroxybenzotriazole, HOBt, and dicyclohexylcarbodiimide, DCC, and an amine, $NHR^4R^5$, in a solvent such as dimethylformamide, DMF, or dichloromethane to give a bis-amide of Formula I.

Compounds of Formula I have also been synthesized using combinatorial techniques, Scheme 2. The diacid chloride is bound to a resin such as Marshall resin to give a bound acid chloride. The bound acid chloride is then reacted with an amine, $NHR^4R^5$, in the presence of triethylamine in a solvent such as DCM to give a resin-bound amide. The resin is then cleaved by reaction with an amine, $NHR^4R^5$, in dioxane in the presence of an organic base to give a bis-amide of Formula I, wherein each $R^4$ and $R^5$ independently are as defined above.

Scheme 1

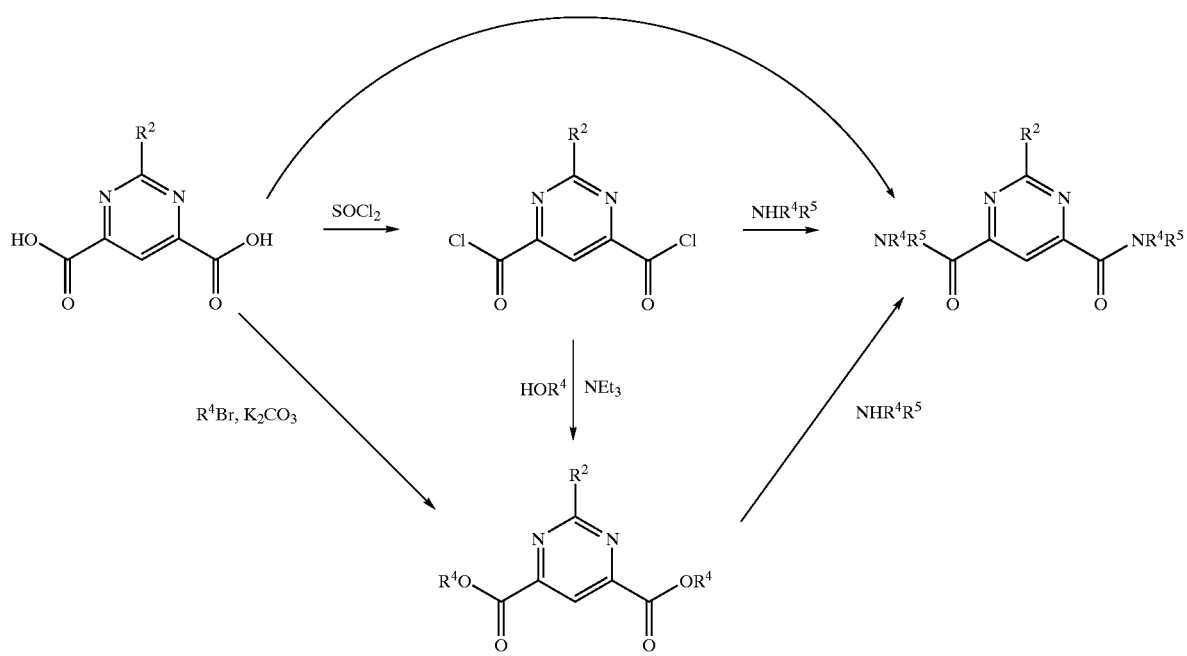

Scheme 2

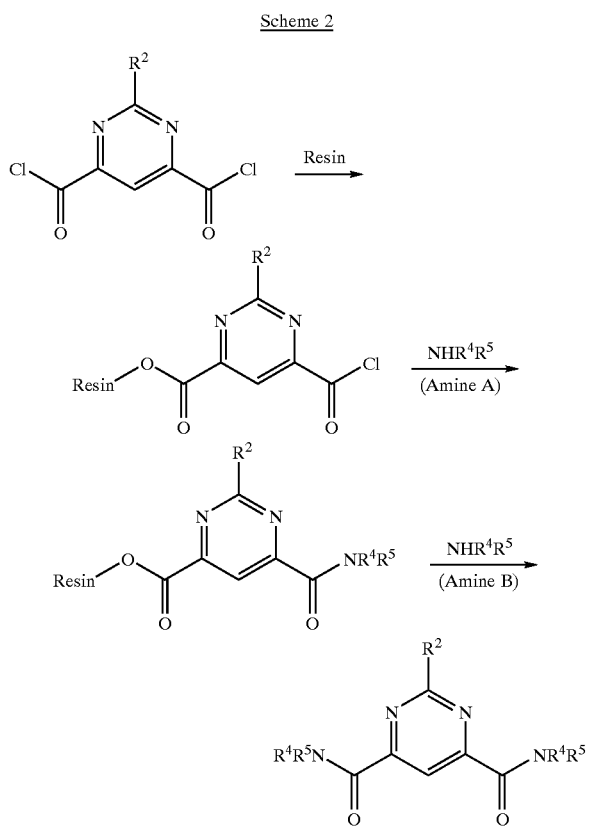

The following detailed examples further illustrate the synthesis of typical invention compounds of Formula I. The examples are representative only, and are not to be construed as limiting the invention in any respect.

EXAMPLE 1

Pyrimidine-4,6-dicarboxylic Acid, Bis-benzylamide

Pyrimidine-4,6-dicarboxylic acid is dissolved in dichloromethane (DCM) at 24° C. To the solution is added three equivalents of thionyl chloride. The reaction mixture is stirred at 24° C. for 1 hour. The reaction mixture is concentrated by evaporation of the solvent under reduced pressure to give an oil. The oil is dissolved in ethyl acetate, and three equivalents of benzylamine are added. The reaction mixture is stirred at 24° C. for 3 hours. The solvent is than removed by evaporation under reduced pressure to give an oil. The oil is purified by chromatography over silica gel, eluting with hexane-ethyl acetate (9:1) to 100% ethyl acetate. The fractions shown by thin layer chromatography to contain a single product component are combined and concentrated to dryness under reduced pressure to give the title compound.

EXAMPLE 2

Combinatorial Synthesis Method

Loading of the Resin is Carried Out as Follows

Marshall resin (15.2 g, 21.25 mmol) is swollen in DCM (300 mL) in a 500-mL resin tube (CAUTION: Slightly exothermic, the DCM may boil), and the mixture is allowed to cool. Once the mixture is cooled, the tube is capped and agitated slowly for 5 minutes, venting frequently. The DCM is drained to waste. The DCM wash is repeated two additional times, then the resin is resuspended in DCM (300 mL), and triethylamine (TEA, 3.2 g, 32 mmol, 1.5 mol. eq.) is added slowly. The resulting mixture is swirled for 5 minutes, and pyrimidine-4,6-dicarboxylic acid dichloride (17.2 g, 85 mmol, 4 eq) is added in one portion. The resin tube is capped, carefully secured in a wrist shaker, and inverted for 36 hours.

After 36 hours, a slight darkening of the resin may be noted. The reaction solvent is drained, and the residual resin is washed three times with DCM (200 mL) and two times with diethyl ether (200 mL). The resin is dried in vacuo for 24 hours. Resin loading is determined both by weight gain and by total chloride determination. Typical loading is about 1.1 mmol/g.

Resin Distribution is Performed as Follows

A Miniblock resin loader is calibrated for each resin used in the protocol. The weight in milligrams of resin added per well is recorded, and the number of millimoles per well of bound pyrimidine-4,6-dicarboxylic acid chloride is calculated. Using this calibration and the loading for each resin, 0.15 mmol of resin is distributed into each reaction tube. The valve on the block is closed.

Amine Solution Prep

An "A" amine set ($NHR^4R^5$) is diluted to 0.5 M in DCM. A 0.2 M solution of TEA in DCM (1.5 mL per reaction) is prepared. A 0.2 M solution of TEA in dioxane (1.5 mL per reaction) is prepared. A "B" amine set ($NHR^4R^5$) is diluted to 0.5 M in dioxane.

Addition of Amine A

The TEA solution in DCM from above (1.5 mL) is added to each reaction tube, then using the Miniblock Map as a guide, the appropriate "A" amine (315 μL, 1.05 eq) is distributed. The mixtures are shaken for 24 hours. After 24 hours, the reaction block is placed on a filtration station without a collection block, and the reactions are drained to waste. The valve is closed, and 2 mL of DCM is added. The mixtures are shaken for 2 minutes, and the reactions are drained to waste again. Unless the following step is to be carried out immediately, the reaction blocks are preferably stored under vacuum.

Addition of Amine B/resin Cleavage

The TEA solution in dioxane from above (1.5 mL) is added to each reaction tube, then using the Miniblock Map as a guide, the appropriate "B" amine (300 μL, 1.05 eq) is distributed. The mixture is shaken for 72 hours. After 72 hours, the reaction block is placed on a filtration station with a labeled collection block, and the reactions are drained. The valve is closed, 2 mL of DCM is added, and the mixture is shaken for 2 minutes. The reactions are drained into the collection tubes.

Analysis

The products in the tubes may be identified by loop mass spectrometry after first evaporating the DCM from the MS samples.

Concentrate

The samples are concentrated in a Genevac.

The invention compounds of Formula I can be evaluated in standard assays for their ability to inhibit the activity of various MMP enzymes. The assays that can be used to evaluate the biological activity of the invention compounds are well known and routinely used by those skilled in the study of MMP inhibitors and their use to treat clinical conditions. The assays measure the amount by which a test compound reduces the hydrolysis of a thiopeptolide substrate catalyzed by a matrix metalloproteinase enzyme. Such assays are described in detail by Ye et al., in *Biochemistry*, 1992;31(45):11231–11235, which is incorporated herein by reference.

Thiopeptolide substrates show virtually no decomposition or hydrolysis in the absence of a matrix metalloproteinase enzyme. A typical thiopeptolide substrate commonly utilized for assays is Ac-Pro-Leu-Gly-thioester-Leu-Leu-Gly-OEt. A 100-$\mu$L assay mixture will contain 50 mM of N-2-hydroxyethylpiperazine-N'-2-ethanesulfonic acid buffer ("HEPES") at pH 7.0, 10 mM CaCl$_2$, 100 $\mu$M thiopeptolide substrate, and 1 mM 5,5'-dithio-bis-(2-nitro-benzoic acid) (DTNB). The thiopeptolide substrate concentration can be varied, for example from 10 to 800 $\mu$M, to obtain Km and Kcat values. The change in absorbance at 405 nm is monitored on a Thermo Max microplate reader (Molecular Devices, Menlo Park, Calif.) at room temperature (22° C.). The calculation of the amount of hydrolysis of the thiopeptolide substrate is based on $E_{412}=13600$ $M^{-1}$ $cm^{-1}$ for the DTNB-derived product 3-carboxy-4-nitrothiophenoxide. Assays can be carried out with and without matrix metalloproteinase inhibitor compounds, and the amount of hydrolysis can be compared for a determination of inhibitory activity of the test compounds.

It should be appreciated that the assay buffer that can be used with stromelysin-1 catalytic domain ("MMP-3CD") is 50 mM of N-morpholinoethane sulfonic acid monohydrate ("MES") at pH 6.0 rather than the HEPES buffer at pH 7.0 described above.

Compounds of Formula I, or a pharmaceutically acceptable salt thereof, are expected to inhibit MMP-13, including MMP-13CD, with $IC_{50}$'s typically in the range of from about 0.001 micromolar to about 10 micromolar, while the compounds are expected to inhibit full length MMP-1, full length MMP-2, MMP-3CD, full length MMP-7, full length MMP-9, MMP-12 catalytic domain, and MMP-14 catalytic domain with $IC_{50}$'s in the range of from about 20 micromolar to greater than 100 micromolar.

The invention compounds of Formula I promise to be potent inhibitors of MMP enzymes and will be especially useful due to their expected selective inhibition of MMP-13. Because of their expected potent and selective inhibitory activity, the invention compounds will be especially useful to treat diseases mediated by the MMP enzymes, and particularly those mediated by MMP-13.

Administration of an invention compound of Formula I, or a pharmaceutically acceptable salt thereof, to a mammal to treat the diseases mediated by MMP enzymes is preferably, although not necessarily, accomplished by administering the compound, or the salt thereof, in a pharmaceutical dosage form.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 to 1000 mg, preferably 10 to 100 mg according to the particular application and the potency of the active component. The composition can, if desired, also contain other compatible therapeutic agents.

In therapeutic use as agents to inhibit a matrix metalloproteinase enzyme for the treatment of atherosclerotic plaque rupture, aortic aneurism, heart failure, restenosis, periodontal disease, corneal ulceration, cancer metastasis, tumor angiogenesis, arthritis, or other autoimmune or inflammatory disorders dependent upon breakdown of connective tissue, the compounds utilized in the pharmaceutical method of this invention are administered at a dose that is effective to inhibit the hydrolytic activity of one or more matrix metalloproteinase enzymes. The initial dosage of about 1 mg/kg to about 100 mg/kg daily will be effective. A daily dose range of about 25 mg/kg to about 75 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired. Typical dosages will be from about 0.1 mg/kg to about 500 mg/kg, and ideally about 25 mg/kg to about 250 mg/kg, such that it will be an amount which is effective to treat the particular disease being prevented or controlled.

The following examples illustrate typical pharmaceutical compositions provided by the invention.

Composition Example 1

Tablet Formulation

| Ingredient | Amount (mg/tablet) |
|---|---|
| Compound of Example 1 | 25 |
| Lactose | 50 |
| Cornstarch (for mix) | 10 |
| Cornstarch (paste) | 10 |
| Magnesium stearate (1%) | 5 |
| Total | 100 |

The compound of Example 1, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of atherosclerosis and arthritis.

Composition Example 2

Preparation for Oral Solution

| Ingredient | Amount |
|---|---|
| Pyrimidine-4,6-dicarboxylic acid, (4-carboxy-benzylamide), [(1,3-benzodioxol-5-ylmethyl)-amide] | 400 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the invention compound named pyrimidine-4,6-dicarboxylic acid, (4-carboxy-benzylamide), [(1,3-benzodioxol-5-ylmethyl)-amide] is dissolved therein. The saccharin, sodium benzoate, flavor, and dye are added and dissolved. The volume is adjusted to 100 mL with distilled water. Each milliliter of syrup contains 4 mg of invention compound.

Composition Example 3

Parenteral Solution

In a solution of 700 mL of propylene glycol and 200 mL of water for injection is suspended 20 g of the invention compound named pyrimidine-4,6-dicarboxylic acid, (4-carboxy-benzylamide), (4-methoxy-benzylamide). After suspension is complete, the pH is adjusted to 6.5 with 1N sodium hydroxide, and the volume is made up to 1000 mL with water for injection. The formulation is sterilized, filled into 5.0-mL ampoules each containing 2.0 mL, and sealed under nitrogen.

As matrix metalloproteinase inhibitors, the compounds of Formula I are useful as agents for the treatment of multiple sclerosis. They are also useful as agents for the treatment of atherosclerotic plaque rupture, restenosis, periodontal disease, corneal ulceration, treatment of burns, decubital ulcers, wound repair, heart failure, cancer metastasis, tumor angiogenesis, arthritis, and other inflammatory disorders dependent upon tissue invasion by leukocytes It should be appreciated that in all invention embodiments described above or in the claims below, whenever an R group such as, for example, $R^1$, $R^2$, $R^3$, $R^4$, $R^5$, or $R^6$, or an n group is used more than once to define an invention compound, each use of the R group is independent of any other use of that same R group or, for that matter, any other R group, unless otherwise specified.

What is claimed is:

1. A compound of Formula IV

IV

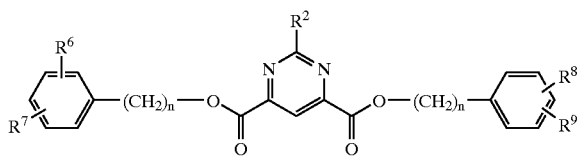

or a pharmaceutically acceptable salt thereof, wherein Each n independently is an integer of from 0 to 6;

$R^2$ is hydrogen, halo, hydroxy, $C_1$–$C_6$ alkyl, $C_1$–$C_6$ alkoxy, $C_2$–$C_6$ alkenyl, $C_2$–$C_6$ alkynyl, $NO_2$, $NR^4R^5$, CN, or $CF_3$; and $R^6$, $R^7$, $R^8$, and $R^9$ independently are hydrogen, halo, $C_1$–$C_6$ alkyl, $C_1$–$C_6$ alkoxy, nitro, or $NH_2$;

$R^4$ and $R^5$ independently are H, $C_1$–$C_6$ alkyl, $C_2$–$C_6$ alkenyl, $C_2$–$C_6$ alkynyl, $(CH_2)_n$ aryl, $(CH_2)_n$ cycloalkyl, $(CH_2)_n$ heteroaryl, or $R^4$ and $R^5$ when taken together with the nitrogen to which they are attached complete a 3- to 8-membered ring containing carbon atoms and optionally containing a heteroatom selected from O, S, or NH, and optionally substituted or unsubstituted.

2. The compound pyrimidine-4,6-dicarboxylic acid bis-(1,3-benzodioxol-5-ylmethyl) ester.

3. A pharmaceutical composition, comprising an MMP-13 inhibiting amount of a compound of claim 1, or a pharmaceutically acceptable salt thereof, together with a pharmaceutically acceptable carrier, diluent, or excipient.

4. A method for treating inflammation, comprising administering to a patient in need of treatment an effective amount of a compound of claim 1, or a pharmaceutically acceptable salt thereof.

5. A method for treating osteoarthritis, comprising administering to a patient in need of treatment an effective amount of a compound of claim 1, or a pharmaceutically acceptable salt thereof.

6. A method for treating rheumatoid arthritis, comprising administering to a patient in need of treatment an effective amount of a compound of claim 1, or a pharmaceutically acceptable salt thereof.

7. A method for treating inflammation, comprising administering to a patient in need of treatment an effective amount of a compound selected from the group consisting of:
Pyrimidine-4,6-dicarboxylic acid, (4-chloro-benzylamide), [(1,3-benzodioxol- 5-ylmethyl)-amide];
Pyrimidine-4,6-dicarboxylic acid, (4-carboxy-benzylamide), [(1,3-benzodioxol- 5-ylmethyl)-amide];
Pyrimidine-4,6-dicarboxylic acid, (4-carboxy-benzylamide), (4-methoxy-benzylamide);
Pyrimidine-4,6-dicarboxylic acid, (4-carboxy-benzylamide), (3-methoxy-benzylamide);
Pyrimidine-4,6-dicarboxylic acid, (4-carbomethoxy-benzylamide), (3-methoxy-benzylamide);
Pyrimidine-4,6-dicarboxylic acid, (4-carboxy-benzylamide), (3-pyridylmethylamide);
Pyrimidine-4,6-dicarboxylic acid, (4-carboxy-benzylamide), (3-thiophenemethylamide);
Pyrimidine-4,6-dicarboxylic acid, (2,1,3-benzothiadiazol-5-ylmethyl)amide, [(1,3-benzodioxol- 5-ylmethyl)-amide];
Pyrimidine-4,6-dicarboxylic acid, (2,1,3-benzooxadiazol-5-ylmethyl)amide, [(1,3-benzodioxol-5-ylmethyl)-amide];
Pyrimidine-4,6-dicarboxylic acid, (2,1,3-benzothiadiazol-5-ylmethyl)amide, (4-methoxy-benzylamide);
Pyrimidine-4,6-dicarboxylic acid, (2,1,3-benzothiadiazol-5-ylmethyl)amide, (3-methoxy-benzylamide);
Pyrimidine-4,6-dicarboxylic acid bis-(1,3-benzodioxol-5-ylmethyl)ester;
Pyrimidine-4,6-dicarboxylic acid, bis-(4-chloro-benzylamide);
Pyrimidine-4,6-dicarboxylic acid, bis-[(1,3-benzodioxol-5-ylmethyl)-amide];
Pyrimidine-4,6-dicarboxylic acid, bis-(4-methoxy-benzylamide);
Pyrimidine-4,6-dicarboxylic acid, bis-(3-methoxy-benxylamide);
Pyrimidine-4,6-dicarboxylic acid, bis-(4-carboxy-benzylamide); and
Pyrimidine-4,6-dicarboxylic acid, bis-(4carbomethoxy-benzylamide), or a pharmaceutically acceptable salt therof.

8. A method for treating osteoarthritis, comprising administering to a patient in need of treatment an effective amount of a compound selected from the group consisting of:
Pyrimidine-4,6-dicarboxylic acid, (4-chloro-benzylamide), [(1,3-benzodioxol-5-ylmethyl)-amide];
Pyrimidine-4,6-dicarboxylic acid, (4-carboxy-benzylamide), [(1,3-benzodioxol-5-ylmethyl)-amide];
Pyrimidine-4,6-dicarboxylic acid, (4-carboxy-benzylamide), (4-methoxy-benzylamide);
Pyrimidine-4,6-dicarboxylic acid, (4-carboxy-benzylamide), (3-methoxy-benzylamide);
Pyrimidine-4,6-dicarboxylic acid, (4-carbomethoxy-benzylamide), (3-methoxy-benzylamide);
Pyrimidine-4,6-dicarboxylic acid, (4-carboxy-benzylamide), (3-pyridylmethylamide);
Pyrimidine-4,6-dicarboxylic acid, (4-carboxy-benzylamide), (3-thiophenemethylamide);
Pyrimidine-4,6-dicarboxylic acid, (2,1,3-benzothiadiazol-5-ylmethyl) amide, [(1,3-benzodioxol-5-ylmethyl)-amide];
Pyrimidine-4,6-dicarboxylic acid, (2,1,3-benzooxadiazol-5-ylmethyl) amide, [(1,3-benzodioxol-5-ylmethyl)-amide];
Pyrimidine-4,6-dicarboxylic acid, (2,1,3-benzothiadiazol-5-ylmethyl) amide, (4-methoxy-benzylamide);
Pyrimidine-4,6-dicarboxylic acid, (2,1,3-benzothiadiazol-5-ylmethyl) amide, (3-methoxy-benzylamide);
Pyrimidine-4,6-dicarboxylic acid bis-(1,3-benzodioxol-5-ylmethyl) ester;
Pyrimidine-4,6-dicarboxylic acid, bis-(4-chloro-benzylamide);
Pyrimidine-4,6-dicarboxylic acid, bis-[(1,3-benzodioxol-5-ylmethyl)-amide];
Pyrimidine-4,6-dicarboxylic acid, bis-(4-methoxy-benzylamide);
Pyrimidine-4,6-dicarboxylic acid, bis-(3-methoxy-benzylamide);
Pyrimidine-4,6-dicarboxylic acid, bis-(4carboxy-benzylamide); and
Pyrimidine-4,6-dicarboxylic acid, bis-(4carbomethoxy-benzylamide), or a pharmaceutically acceptable salt thereof.

9. A method for treating rheumatoid arthritis, comprising administering to a patient in need of treatment an effective amount of a compound selected from the group consisting of:
Pyrimidine-4,6-dicarboxylic acid, (4-chloro-benzylamide), [(1,3-benzodioxol-5- ylmethyl)-amide];
Pyrimidine-4,6-dicarboxylic acid, (4-carboxy-benzylamide, [(1,3-benzodioxol-5-ylmethyl)-amide];
Pyrimidine-4,6-dicarboxylic acid, (4-carboxy-benzylamide), (4-methoxy-benzylamide);
Pyrimidine-4,6-dicarboxylic acid, (4-carboxy-benzylamide), (4-methoxy-benzylamide);
Pyrimidine-4,6-dicarboxylic acid, (4-carboxy-benzylamide), (3-methoxy-benzylamide);
Pyrimidine-4,6-dicarboxylic acid, (4-carbomethoxy-benzylamide), (3-methoxy-benzylamide);
Pyrimidine-4,6-dicarboxylic acid, (4-carboxy-benzylamide), (3-pyridylmethylamide);
Pyrimidine-4,6-dicarboxylic acid, (4-carboxy-benzylamide), (3-thiophenemethylamide);
Pyrimidine-4,6-dicarboxylic acid, (2,1,3-benzothiadiazol-5-ylmethyl) amide, [(1,3-benzodioxol-5-ylmethyl)-amide];
Pyrimidine-4,6-dicarboxylic acid, (2,1,3-benzooxadiazol-5-ylmthyl) amide, [(1,3-benzodioxol-5-ylmethyl)-amide];
Pyrimidine-4,6-dicarboxylic acid, (2,1,3-benzothiadiazol-5-ylmethy) amide, (4methoxy-benzylamide);
Pyrimidine-4,6-dicarboxylic acid, (2,1,3-benzothiadiazol-5-ylmethyl) amide, (3-methoxy-benzylamide);

Pyrimidine-4,6-dicarboxylic acid bis-(1,3-benzodioxol-5-ylmethyl) ester;

Pyrimidine-4,6-dicarboxylic acid, bis-(4-chloro-benzylamide);

Pyrimidine-4,6-dicarboxylic acid, bis-[(1,3-benzodioxol-5-ylmethyl)-amide];

Pyrimidine-4,6-dicarboxylic acid, bis-(4-methoxy-benzylamide);

Pyrimidine-4,6-dicarboxylic acid, bis-(3-methoxy-benzylamide);

Pyrimidine-4,6-dicarboxylic acid, bis-(4-carboxy-benzylamide); and

Pyrimidine-4,6-dicarboxylic acid, bis-(4-carbomethoxy-benzylamide), or a pharmaceutically acceptable salt thereof.

\* \* \* \* \*